（12）United States Patent
Hoss et al.

(10) Patent No.: US 9,724,029 B2
(45) Date of Patent: *Aug. 8, 2017

(54) ANALYTE MONITORING DEVICE AND METHODS

(71) Applicant: Abbott Diabetes Care Inc., Alameda, CA (US)

(72) Inventors: Udo Hoss, Castro Valley, CA (US); Benjamin J. Feldman, Berkeley, CA (US); Zenghe Liu, Alameda, CA (US); Hyun Cho, Berkeley, CA (US); Benjamin M. Rush, Oakland, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 14/629,171

(22) Filed: Feb. 23, 2015

(65) Prior Publication Data

US 2015/0173657 A1 Jun. 25, 2015

Related U.S. Application Data

(63) Continuation of application No. 13/087,190, filed on Apr. 14, 2011, now Pat. No. 8,965,477.

(Continued)

(51) Int. Cl.
*A61B 5/1473* (2006.01)
*A61B 5/1468* (2006.01)
(Continued)

(52) U.S. Cl.
CPC ........ *A61B 5/1473* (2013.01); *A61B 5/14532* (2013.01); *A61B 5/7275* (2013.01);
(Continued)

(58) Field of Classification Search
CPC .... A61B 2560/0252; A61B 2560/0443; A61B 5/1451; A61B 5/14532; A61B 5/1473;
(Continued)

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |

(Continued)

*Primary Examiner* — Navin Natnithithadha
(74) *Attorney, Agent, or Firm* — Arent Fox LLP (57) ABSTRACT

Method and system for determining real time analyte concentration including an analyte sensor having a portion in fluid contact with an interstitial fluid under a skin layer, an on-body electronics including a housing coupled to the analyte sensor and configured for positioning on the skin layer, the on-body electronics housing including a plurality of electrical contacts, on the housing; and a data analysis unit having a data analysis unit housing and a plurality of probes, on the housing. Each of the probes configured to electrically couple to a respective electrical contact when the data analysis unit is positioned in physical contact with the on-body electronics. The one or more signals on the probes correspond to one or more of a substantially real time monitored analyte concentration level (MACL), MACL over a predetermined time period, or a rate of change of the MACL, or combinations thereof, are provided.

14 Claims, 3 Drawing Sheets

Related U.S. Application Data (60) Provisional application No. 61/422,490, filed on Dec. 13, 2010, provisional application No. 61/325,260, filed on Apr. 16, 2010.

(51) Int. Cl.
*A61B 5/00* (2006.01)
*A61B 5/145* (2006.01)

(52) U.S. Cl.
CPC ............ *A61B 5/742* (2013.01); *A61B 5/7405* (2013.01); *A61B 5/7455* (2013.01); *A61B 5/1451* (2013.01); *A61B 5/1468* (2013.01); *A61B 2560/0252* (2013.01); *A61B 2560/0443* (2013.01)

(58) Field of Classification Search
CPC ..... A61B 5/7275; A61B 5/7405; A61B 5/742; A61B 5/7455; A61B 5/1468
USPC .......................................... 600/309, 345–366
See application file for complete search history.

(56) References Cited

U.S. PATENT DOCUMENTS

| | | | |
|---|---|---|---|
| 5,112,455 A | 5/1992 | Cozzette et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,320,715 A | 6/1994 | Berg | |
| 5,344,754 A | 9/1994 | Zweig | |
| 5,509,410 A | 4/1996 | Hill et al. | |
| 5,543,326 A | 8/1996 | Heller et al. | |
| 5,593,852 A | 1/1997 | Heller et al. | |
| 5,601,435 A | 2/1997 | Quy | |
| 5,628,890 A | 5/1997 | Carter et al. | |
| 5,660,163 A | 8/1997 | Schulman et al. | |
| 5,800,420 A * | 9/1998 | Gross | A61K 9/0021 204/280 |
| 5,807,375 A * | 9/1998 | Gross | A61K 9/0021 600/309 |
| 5,820,551 A | 10/1998 | Hill et al. | |
| 5,820,622 A * | 10/1998 | Gross | A61K 9/0021 204/280 |
| 5,822,715 A | 10/1998 | Worthington et al. | |
| 5,899,855 A | 5/1999 | Brown | |
| 5,918,603 A | 7/1999 | Brown | |
| 6,071,391 A | 6/2000 | Gotoh et al. | |
| 6,103,033 A | 8/2000 | Say et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,144,837 A | 11/2000 | Quy | |
| 6,161,095 A | 12/2000 | Brown | |
| 6,175,752 B1 | 1/2001 | Say et al. | |
| 6,270,455 B1 | 8/2001 | Brown | |
| 6,275,717 B1 * | 8/2001 | Gross | A61B 5/14865 600/309 |
| 6,284,478 B1 | 9/2001 | Heller et al. | |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,424,847 B1 | 7/2002 | Mastrototaro et al. | |
| 6,461,496 B1 | 10/2002 | Feldman et al. | |
| 6,503,381 B1 | 1/2003 | Gotoh et al. | |
| 6,514,460 B1 | 2/2003 | Fendrock | |
| 6,514,718 B2 | 2/2003 | Heller et al. | |
| 6,540,891 B1 | 4/2003 | Stewart et al. | |
| 6,560,471 B1 | 5/2003 | Heller et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,600,997 B2 | 7/2003 | Deweese et al. | |
| 6,605,200 B1 | 8/2003 | Mao et al. | |
| 6,605,201 B1 | 8/2003 | Mao et al. | |
| 6,616,819 B1 | 9/2003 | Liamos et al. | |
| 6,618,934 B1 | 9/2003 | Feldman et al. | |
| 6,641,533 B2 | 11/2003 | Causey, III et al. | |
| 6,650,471 B2 | 11/2003 | Doi | |
| 6,654,625 B1 | 11/2003 | Say et al. | |
| 6,676,816 B2 | 1/2004 | Mao et al. | |
| 6,730,200 B1 | 5/2004 | Stewart et al. | |
| 6,736,957 B1 | 5/2004 | Forrow et al. | |
| 6,746,582 B2 | 6/2004 | Heller et al. | |
| 6,749,740 B2 | 6/2004 | Liamos et al. | |
| 6,764,581 B1 | 7/2004 | Forrow et al. | |
| 6,773,671 B1 | 8/2004 | Lewis et al. | |
| 6,881,551 B2 | 4/2005 | Heller et al. | |
| 6,893,545 B2 | 5/2005 | Gotoh et al. | |
| 6,932,892 B2 | 8/2005 | Chen et al. | |
| 6,932,894 B2 | 8/2005 | Mao et al. | |
| 6,942,518 B2 | 9/2005 | Liamos et al. | |
| 7,167,818 B2 | 1/2007 | Brown | |
| 7,295,867 B2 | 11/2007 | Berner et al. | |
| 7,299,082 B2 | 11/2007 | Feldman et al. | |
| 7,697,967 B2 | 4/2010 | Stafford | |
| 8,965,477 B2 * | 2/2015 | Hoss | A61B 5/14532 600/345 |
| 2004/0073095 A1 | 4/2004 | Causey, III et al. | |
| 2004/0186365 A1 | 9/2004 | Jin et al. | |
| 2005/0182306 A1 | 8/2005 | Sloan et al. | |
| 2007/0038053 A1 | 2/2007 | Berner et al. | |
| 2007/0056858 A1 | 3/2007 | Chen et al. | |
| 2007/0068807 A1 | 3/2007 | Feldman et al. | |
| 2007/0221497 A1 | 9/2007 | Egawa et al. | |
| 2007/0227911 A1 | 10/2007 | Wang et al. | |
| 2007/0233013 A1 | 10/2007 | Schoenberg | |
| 2008/0081977 A1 | 4/2008 | Hayter et al. | |
| 2008/0161666 A1 | 7/2008 | Feldman et al. | |
| 2009/0054748 A1 | 2/2009 | Feldman et al. | |
| 2009/0076360 A1 | 3/2009 | Brister et al. | |
| 2009/0216105 A1 | 8/2009 | Drucker et al. | |
| 2009/0247857 A1 | 10/2009 | Harper et al. | |
| 2009/0292188 A1 | 11/2009 | Hoss et al. | |
| 2009/0294277 A1 | 12/2009 | Thomas et al. | |
| 2010/0081909 A1 | 4/2010 | Budiman et al. | |
| 2010/0137695 A1 | 6/2010 | Yodfat et al. | |
| 2010/0198034 A1 | 8/2010 | Thomas et al. | |
| 2010/0198142 A1 | 8/2010 | Sloan et al. | |
| 2010/0204557 A1 | 8/2010 | Kiaie et al. | |
| 2010/0213057 A1 | 8/2010 | Feldman et al. | |
| 2010/0230285 A1 | 9/2010 | Hoss et al. | |
| 2010/0326842 A1 | 12/2010 | Mazza et al. | |
| 2011/0021889 A1 | 1/2011 | Hoss et al. | |
| 2011/0029269 A1 | 2/2011 | Hayter et al. | |
| 2011/0213225 A1 | 9/2011 | Bernstein et al. | |
| 2011/0257495 A1 * | 10/2011 | Hoss | A61B 5/14532 600/347 |
| 2012/0232520 A1 | 9/2012 | Sloan et al. | |

* cited by examiner

ANALYTE MONITORING DEVICE AND METHODS

CROSS-REFERENCE TO RELATED APPLICATIONS

This application is a continuation of U.S. patent application Ser. No. 13/087,190, filed on Apr. 14, 2011, which claims priority to U.S. Provisional Application No. 61/325,260, filed Apr. 16, 2010 and U.S. Provisional Application No. 61/422,490, filed Dec. 13, 2010, the disclosures of which are herein incorporated by reference in their entirety.

This application is related to U.S. patent application Ser. No. 12/393,921, filed Feb. 26, 2009; U.S. patent application Ser. No. 12/807,278, filed Aug. 31, 2010; U.S. patent application Ser. No. 12/876,840, filed Sep. 7, 2010; U.S. Provisional Application No. 61/325,155, filed Apr. 16, 2010; and U.S. Provisional Application No. 61/247,519, filed Sep. 30, 2009. The disclosures of the above-mentioned applications are incorporated herein by reference in their entirety.

BACKGROUND

Diabetes Mellitus is an incurable chronic disease in which the body does not produce or properly utilize insulin. Insulin is a hormone produced by the pancreas that regulates blood glucose. In particular, when blood glucose levels rise, e.g., after a meal, insulin lowers the blood glucose levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

People suffering from diabetes often experience long-term complications. Some of these complications include blindness, kidney failure, and nerve damage. Additionally, diabetes is a factor in accelerating cardiovascular diseases such as atherosclerosis (hardening of the arteries), which often leads stroke, coronary heart disease, and other diseases, which can be life threatening.

The severity of the complications caused by both persistent high glucose levels and blood glucose level fluctuations has provided the impetus to develop diabetes management systems and treatment plans. In this regard, diabetes management plans historically included multiple daily testing of blood glucose levels typically by a finger-stick to draw and test blood. The disadvantage with finger-stick management of diabetes is that the user becomes aware of his blood glucose level only when he performs the finger-stick. Thus, blood glucose trends and blood glucose snapshots over a period of time is unknowable. More recently, diabetes management has included the implementation of glucose monitoring systems. Glucose monitoring systems have the capability to continuously monitor a user's blood glucose levels. Thus, such systems have the ability to illustrate not only present blood glucose levels but a snapshot of blood glucose levels and blood glucose fluctuations over a period of time.

SUMMARY

Embodiments of the present disclosure includes a transcutaneously positionable analyte sensor in signal communication with electronics which process signals from the analyte sensor transfer or otherwise provide the processed signals related to monitored analyte level to a receiver unit, a blood glucose meter or other devices configured to receive, process, analyze, output, display and/or store the processed signals. Embodiments of the analyte monitoring systems include in vivo analyte sensors in fluid contact with body fluid such as interstitial fluid to monitor the analyte level such as glucose. Embodiments include electronics and/or data processing, storage and/or communication components that are electrically coupled to the analyte sensor, and may include a housing that is placed or positioned on the body surface such as on the skin surface and adhered thereon with an adhesive and retained and maintained in the adhered position for the duration of the analyte monitoring time period using the analyte sensor such as, for example, about 15 days or more, about 10 days or more, about 7 days or more, or about 5 days or more, or about 3 days or more. The housing including the electronics and/or data processing, storage and/or data communication components may be positioned on discrete on-body locations including under clothing during the duration of the monitoring time period. The analyte monitoring device that is coupled to the body and includes the transcutaneously positionable analyte sensor, housing, and electronics and/or data processing, storage and/or communication components, is also referred to herein as an "on-body unit", "OBU", "on body patch", or "patch".

The particular profile, as well as the height, width, length, weight, and volume of the housing may vary and depends, at least in part, on the components and associated functions included in the OBU. In general, the OBU includes a housing typically formed as a single integral unit that rests on the skin of the patient. The housing typically contains most or all of the electronic components of the OBU. The housing may be made from a variety of materials such as, but not limited to, metal, metal-alloys, natural or synthetic polymers, etc. For example, plastics such as rigid thermoplastics and engineering thermoplastics may be used. Additional examples of suitable materials include, for instance, polyvinyl chloride, polyethylene, polypropylene, polystyrene, ABS polymers, and copolymers thereof. The housing of the OBU may be formed using a variety of techniques including, for example, injection molding, compression molding, casting, and other molding methods.

Embodiments include the housing of the on body patch or housing of the electronics that is water proof such that the user or the patient wearing the housing on a discrete on-body location may swim, shower, exercise or otherwise engage in daily activities with comfort and without inconvenience. Embodiments include the adhesive provided on the bottom surface of the housing in contact with the skin surface that retains the housing in position on the skin surface during the duration of the analyte monitoring time period discussed above.

Embodiments of the present disclosure include electrical contacts on the surface of the housing that includes the electronics and/or data processing, storage and/or communication components which are electrically coupled to the analyte sensor such that when electrical contacts or probes provided on the receiver unit or the blood glucose meter are in physical contact with the corresponding electrical contacts on the surface of the housing that includes the electronics and/or data processing, storage and/or communication components, signals associated with the monitored analyte level by the analyte sensor are acquired by the receiver unit or the blood glucose meter. The receiver unit may also be referred to herein as "reader" or "reader unit". As described above, the reader may be an analyte monitoring device that is brought in contact with the OBU to acquire readings from the OBU. The reader may be, for example, an analyte meter (e.g., blood glucose meter), a mobile device that has been adapted to receive readings from the OBU, etc.

Details of embodiments including analyte data acquisition by physically contacting or touching the housing of the sensor electronics with the reader or the blood glucose meter is provided in U.S. Provisional Application No. 61/247,519, the disclosure of which is incorporated herein by reference for all purposes. In this manner, embodiments of the present disclosure include analyte data acquisition or ability to obtain real time glucose data by physically touching or contacting the reader or the blood glucose meter to the housing of the electronics and/or data processing, storage and/or communication components.

Embodiments of the present disclosure include analyte sensors that are self-powered such that an external power source such as a battery is unnecessary to have the analyte sensor generate a signal that is proportional to the monitored analyte concentration. Detailed description of embodiments of such self-powered sensor is provided in U.S. patent application Ser. No. 12/393,921 filed Feb. 26, 2009, the disclosure of which is incorporated herein by reference for all purposes. The absence of the external power source such as a battery (or the reduction in size of the external power source required) provides embodiments of the present disclosure with the size and/or the form factor of the housing for the electronics and/or data processing, storage and/or communication components to be small (for example, approximately the size of a dime—about 18 mm in diameter) that is comfortable to wear on the skin surface during the approximately 10 days of wear on the skin surface.

Embodiments of the present disclosure include real time analyte data acquisition by physical contact between the reader or the blood glucose meter and the on body housing coupled to the analyte sensor, where signals are provided to the reader or the blood glucose meter that are associated with the real time analyte concentration (such as the real time glucose value) and/or monitored analyte concentration trend information for a predetermined time period (such as for example, the past 3 hours of glucose concentration that are monitored by the analyte sensor and stored by the electronics and/or data processing, storage and/or communication components in the housing). Embodiments also include storing and providing trend information with the real time monitored analyte concentration where the predetermined time period may be about 1 hour, about 2 hours, about 5 hours or more.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. Nos. 12/131,012; 12/242,823; 12/363,712; 12/495,709; 12/698,124; 12/699,653; 12/699,844; and 12/714,439 and U.S. Provisional Application Ser. Nos. 61/230,686 and 61/227,967.

DETAILED DESCRIPTION

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Figure 1:
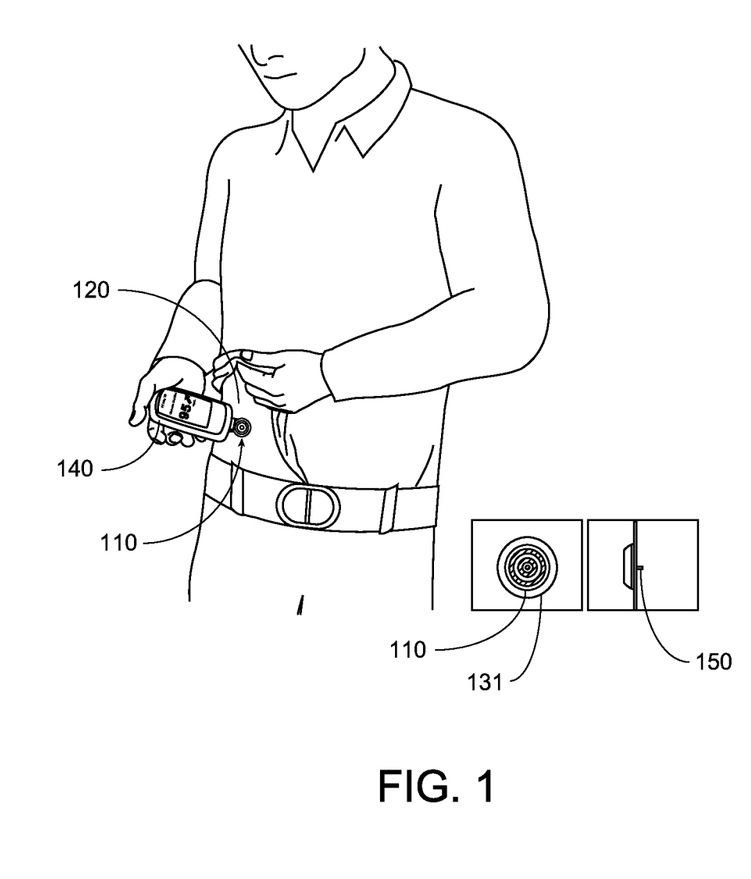
FIG. 1 illustrates an overall system of the analyte monitoring system including real time data acquisition in embodiments of the present disclosure.

FIG. 1 illustrates an overall system of the analyte monitoring system including real time data acquisition in embodiments of the present disclosure. Referring to FIG. 1 analyte monitoring system 100 of one embodiment of the present disclosure is shown. In particular, as shown, in one embodiment, the on-body housing 110 is positioned or adhered to the skin surface 120 of the user or the patient using, for example, an adhesive 131 to retain the position of the on-body housing 110 on the skin surface during the monitoring time period such as, for example, about 10 days or more. Referring to FIG. 1, as shown, when the user or the patient wishes to determine the analyte concentration, the reader or the blood glucose meter 140 is positioned such that it contacts or touches the on-body housing 110 as shown. In certain embodiments, the physical contact or touching of the on-body housing 110 with the reader or the blood glucose meter 140 transfers one or more signals from the electronics contained within the on-body housing 110 to the reader or the blood glucose meter 140 via electrical communication. The transferred or provided signals may include signals corresponding to the real time analyte concentration level such as, for example, real time glucose level information, monitored analyte concentration trend information such as, for example but not limited to, the previous three hours, the rate of change of the analyte concentration determined based at least in part of the monitored analyte concentration trend information, or one or more combinations thereof.

Referring again to FIG. 1, it can be seen from the middle insert figure that an analyte sensor 150 may be transcutaneously positioned such that a portion of the analyte sensor is positioned and retained under the skin layer during the monitoring time period of approximately, for example, but not limited to ten days, and further, that the analyte sensor 150 is coupled to the on-body housing 110 such that the electrodes (working and counter electrodes, for example) of the analyte sensor 150 are electrically coupled to one or more electrical components or sensor electronics in the on-body housing 110 and configured to process and store, among others, the signals from the analyte sensor 150. Furthermore, by way of nonlimiting comparison, as discussed above, embodiments including self-powered analyte sensor which in some embodiments does not need an external power supply and the touch based analyte data acquisition/communication with obviates the need for a wireless data communication component, permits the sizing of the on-body housing 110 to be approximately the size of a dime. After the monitoring time period, the analyte sensor 150 and/or on-body housing 110 may be removed, disposed, and replaced.

Electrodes may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

Figure 2:
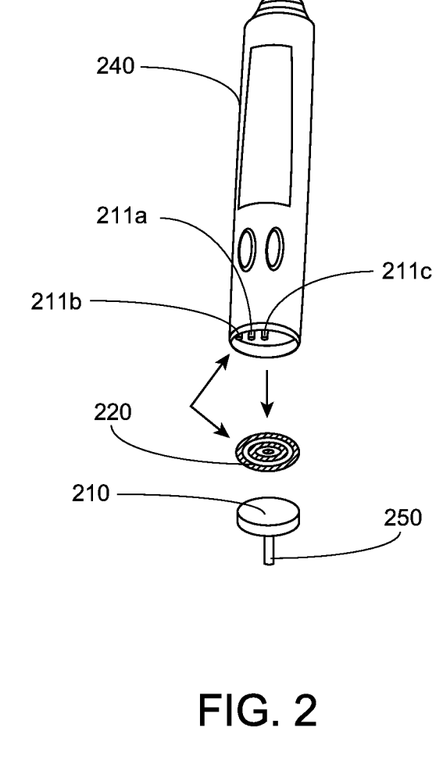
FIG. 2 illustrates the components of an analyte monitoring system in accordance with an embodiment of the present disclosure.

FIG. 2 illustrates the components of the analyte monitoring system in accordance with an alternative embodiment of the present disclosure. Referring to FIG. 2, as shown, embodiments include a reader or blood glucose meter 240 that is provided with probes 211a, 211b, 211c configured to make electrical contact with the respective one of the concentric electrical contacts 220 on the on-body housing 210 connected to an analyte sensor 250. As can be seen, embodiments include the probes 211a, 211b, 211c at a predetermined position on the housing of the reader or the blood glucose meter 240, and at a position relative to each other such that when the reader or the blood glucose meter 240 is positioned in contact with the on-body housing 210, each of the probes 211a, 211b, 211c of the reader or the blood glucose meter 240 make physical contact with the respective one of the concentric electrical contacts 220 on the on-body housing 210.

The analyte sensor 250 extends from the on-body housing 210 to transcutaneously position electrodes (e.g., working and counter electrodes) on the analyte sensor 250 under the skin layer of a user. The electrodes of the analyte sensor 250 are electrically coupled to one or more electrical components or sensor electronics in the on-body housing 210. Such sensor electronics are configured to process and store the signals from the analyte sensor 250. After the monitoring time period, the analyte sensor 250 and/or on-body housing 210 may be removed, disposed, and replaced.

Referring to FIG. 2, while embodiments include concentric electrical contacts configuration on the on-body housing 210, in accordance with the embodiments of the present disclosure, the electrical contacts may include other shapes and sizes such as spaced apart probes, contact pads, oval shaped contacts, and any other suitable configuration to easily establish the electrical contact with the respective of the probes 211a, 211b, 211c on the reader or the blood glucose meter 240 when the reader or the blood glucose meter 240 is brought into contact with the on-body housing 210.

It should be appreciated that the shape and position of the corresponding contacts on the reader may vary in different embodiments but should enable appropriate contact with the arrangement of concentric electrical contacts 220 when the reader is brought in contact with the OBU. The concentric shape of the electrical contacts 220 enable a non-specific orientation to be achieved. In other words, the reader may be placed on the OBU irrespective of orientation and still provide contact with the electrical contacts on the OBU. For example, in some embodiments, the reader includes concentric electrical contacts that line up with the concentric electrical contacts on the OBU. For instance, the reader may include ring-shaped concentric electrical contacts with the same diameter as the corresponding electrical contacts on the OBU. Or as another example, the reader may include electrical contacts that are not ring shaped but disposed at the appropriate distance to come in contact with the corresponding concentric electrical contacts on the OBU when the reader is coupled with the OBU. For instance, a single contact point may be used on the reader that is disposed at the appropriate location to align with the diameter of a ring-shaped electrical contact on the OBU. In this way, regardless of the orientation of the reader on the OBU, the contact point will always align with the diameter of the ring-shaped electrical contact.

It should be appreciated that, in some embodiments, the reader may include more than one contact for a corresponding electrical contact on the OBU. For example, the reader may include two or more contacts that are disposed at the appropriate location on the reader to align with the diameter of a ring-shaped concentric electrical contact. This provides additional assurance of a good connection as well. Furthermore, it should be appreciated that, in some embodiments, the reader may include an interface that is designed to physically mate with or "fit" with the OBU to further promote a good electrical connection.

It should also be appreciated that, in some embodiments, the concentric electrical contacts may be disposed on the reader, and the OBU may be include various shaped and positioned electrical contacts that align with the concentric electrical contacts on the reader.

Figure 3:
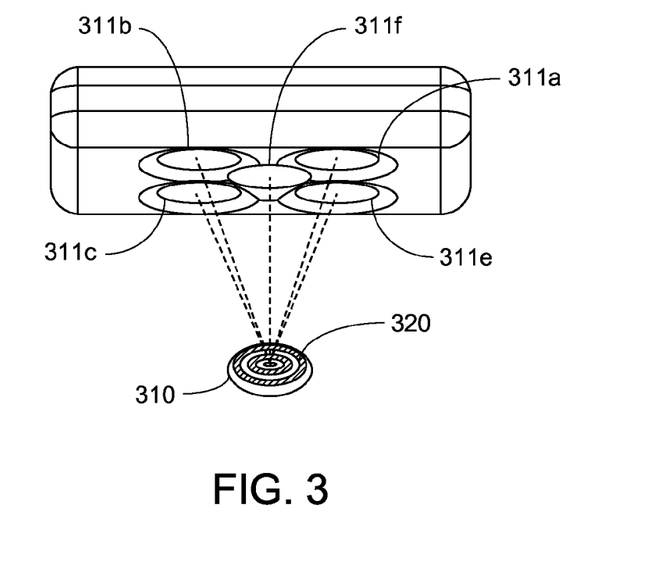
FIG. 3 illustrates the on body housing electrical contacts coupleable to the analyte sensor electrodes in an analyte monitoring system in accordance with an embodiment of the present disclosure.

FIG. 3 illustrates the on-body housing electrical contacts coupleable to the analyte sensor electrodes in an analyte monitoring system in accordance with one embodiment of the present disclosure. Referring to FIG. 3, embodiments of the present disclosure include the reader or the blood glucose meter having a plurality of mating or contact sites 311a, 311b, 311c, 311d, 311e, where each of the plurality of contact sites 311a, 311b, 311c, 311d, 311e include probes to establish electrical contact with the corresponding one of the concentric electrical contacts 320 on the on-body housing 310. That is, in certain embodiments, to facilitate alignment of the probes of the reader or the blood glucose meter to the concentric electrical contacts 320 of the on-body housing 310, the reader or the blood glucose meter may be provided with multiple contact sites 311a, 311b, 311c, 311d, 311e such that any one of the five contact sites 311a, 311b, 311c, 311d, 311e shown in FIG. 3 may transfer the analyte sensor generated signals from to the reader or the blood glucose meter. In this way, the user may more easily couple the reader to the OBU with a successful connection since there are more connection sites for the user to mate the OBU with. It should be appreciated that any number of contact sites may be implemented in various embodiments. Further, in some embodiments, the plurality of contact sites may be configured to cover a large portion of one side of the reader, to further facilitate a successful connection. For example, in some instance, the plurality of contact sites may cover 50% or more of the reader when viewed from one side, such as 75% or more, and including 90% or more.

In certain embodiments, the plurality of contact sites 311a, 311b, 311c, 311d, 311e may be provided on an outer housing surface of the reader or the blood glucose meter, where each of the plurality of contact sites 311a, 311b, 311c, 311d, 311e are beveled or include a groove so as to facilitate the mating with the respective concentric electrical contacts on the on-body housing. Embodiments also includes geometries and/or configurations of the mating sites on the reader or the blood glucose meter and/or the on-body housing with the electrical contacts to facilitate and/or aid the physical connection between the two components during analyte sensor data acquisition to determine real time analyte concentration level and/or trend information. For example, each contact site 311a, 311b, 311c, 311d, 311e of the reader or the blood glucose meter may include a rail or protrusion that aligns with a corresponding respective groove on the on-body housing 310 to guide, aid, and/or facilitate the alignment or proper positioning of the contact probes on the reader or blood glucose meter to the respective concentric electrical contacts on the on-body housing 310. Such a groove on the on body housing 310 in certain embodiments may minimize interference and/or discomfort while wearing the on-body housing on the skin surface during the monitoring time period of for example, about ten days.

Figure 4:
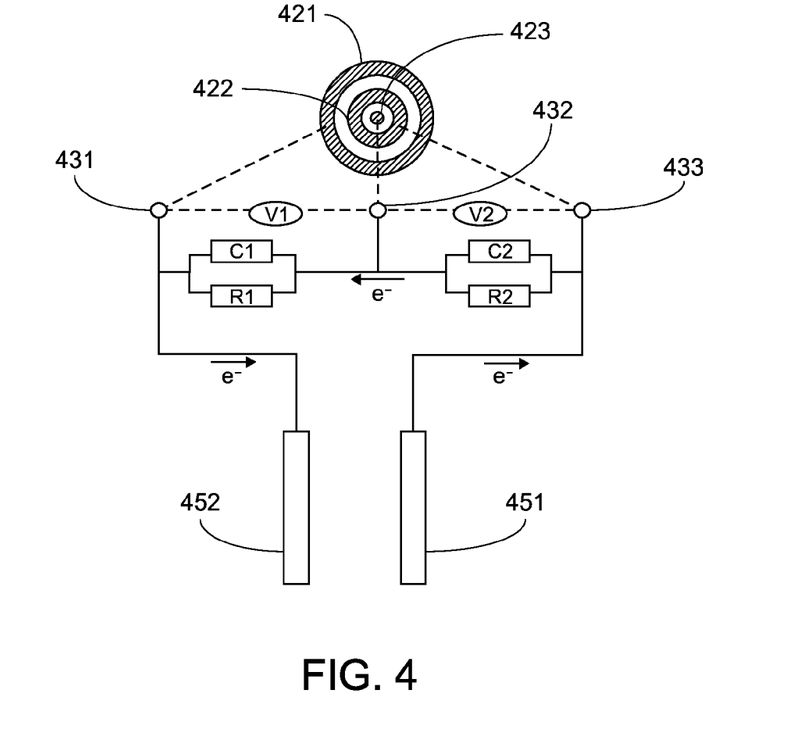
FIG. 4 illustrates the concentric electrical contacts on the on-body housing electrically coupled to the analyte sensor in embodiments of the present disclosure.

FIG. 4 illustrates the concentric electrical contacts on the on-body housing electrically coupled to the analyte sensor in embodiments of the present disclosure. Referring to FIG. 4, embodiments include concentric electrical contacts 421, 422, 423 each coupled to a respective node or terminal 431, 432, 433 in the electronics of the on-body housing, which is also coupled to the analyte sensor including the working electrode 451 and the counter electrode 452. As shown in FIG. 4, two resistor-capacitor (RC) pairs R1/C1 and R2/C2 are provided in series and connected between the working electrode 451 and the counter electrode 452 of the transcutaneously positionable analyte sensor. Measurements for voltages V1 and V2 indicative of the analyte concentration detected by the analyte sensor may be obtained by determining the voltage between nodes 431 and 432 for voltage V1 and between nodes 432 and 433 for voltage V2, where nodes 431, 432, and 433 are respectively coupled to the outer concentric electrical contact 421, the middle concentric electrical contact 422, and the inner concentric electrical contact 423 as in the embodiment shown in FIG. 4.

Referring still to FIG. 4, it can be seen that the resistors R1, R2 may be either resistors or thermistors. Embodiments include approximate resistance value of resistors R1 and R2 (or embodied as thermistors) at room temperature (approximately 25° C.) is approximately 5 MΩ. Embodiments include such relatively high resistance values to increase the voltage signal across the working and counter electrodes 451, 452.

Figure 5:
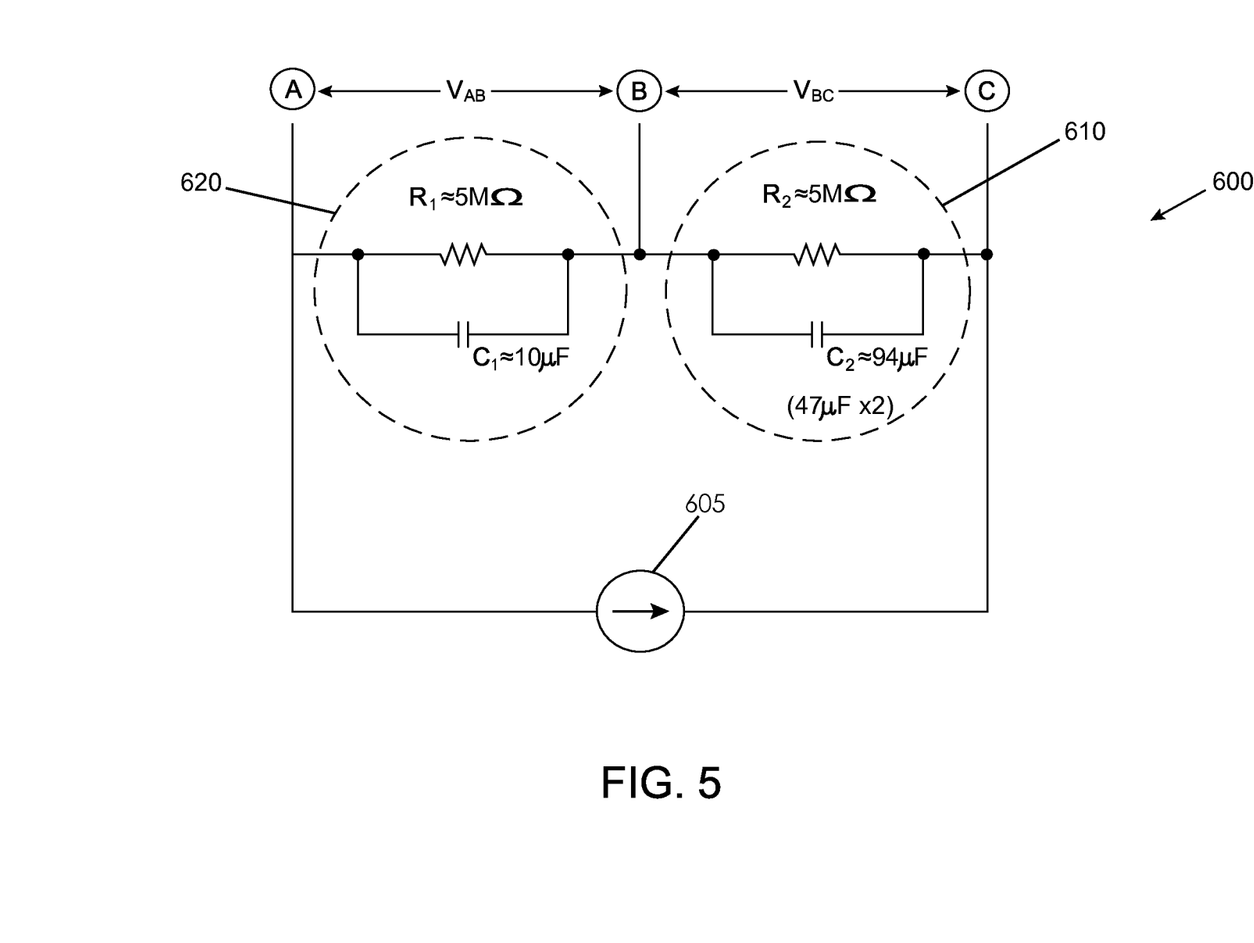
FIG. 5 illustrates a circuit diagram representation of an example OBU having a self-powered sensor, according to certain embodiments

FIG. 5 illustrates a circuit diagram representation of an example OBU having a self powered sensor, according to certain embodiments. As shown, the electronics within the OBU includes two resistor-capacitor (RC) pairs 610 and 620 that are provided in series. RC pair 620 is shown comprising R1 in parallel with C1. RC pair 610 is shown comprising R2 in parallel with C1. In the example shown, resistor R1 is approximately 5 MΩ and capacitor C1 is approximately 10 µF; and resistor R2 is approximately 5 MΩ and capacitor C2 is approximately 94 µF. The embodiment shown includes approximate resistance values of resistors R1 and R2 at room temperature (approximately 25° C.). Some embodiments include such relatively high resistance values to increase the voltage signal across the working and counter electrodes of the analyte sensor. It should be appreciated that the values shown are exemplary and that other values may be implemented in other embodiments. Furthermore, it should be appreciated that C2 may be provided by one or more capacitors, and R1, R2 may be implemented as resistors or thermistors.

Node A is shown at one end of the first RC pair; node B between the two RC pairs; and node C at the other end of the second RC pair. Current source 605 is shown across nodes A and C and represents the current flow provided to circuit 600 by the analyte sensor when contacting interstitial fluid under a skin layer, for example.

The working electrode of the analyte sensor is electrically connected to node A, and the counter electrode of the analyte sensor is electrically connected to node B. When the transcutaneously positionable sensor contact interstitial fluid, for example, current flow is generated from the resulting chemical reaction that takes place. For example, current within the nanoamp (nA) range may be generated and provided to the RC pairs of the electronic circuit.

Concentric electrical contacts (not shown) disposed externally on the housing of the OBU are each coupled to a respective node A, B, and C in the electronic circuit shown. In this way, one concentric electrical contact is provided at the working electrode (node A), another concentric electrical contact at the counter electrode (node C), and yet another concentric electrical contact between the two RC pairs (node B).

The circuit shown enables measurements to be taken that are indicative of analyte concentrations detected by the analyte sensor. Vab is the voltage across the first RC pair (e.g., across nodes A and B) and reflects the current glucose measurement, as filtered based on the R1*C1 time constant. Vbc is the voltage across the second RC pair (e.g., across nodes B and C) and reflects the average glucose value over a longer period of time, as determined by the R2*C2 time constant. Furthermore, the difference between the two voltage readings Vab and Vbc represents trend information for the detected analyte concentrations.

In many instances, the measurement accuracy of analyte sensors is dependent upon temperature. As such, in one embodiment, a temperature sensor is provided with the on-body component to measure body temperature at or near the analyte sensor. The temperature reading can then be used to calibrate the measurement readings accordingly. The temperature sensor may be internal or external to the on-body housing. The temperature sensor may also sit above the skin, or be provided as an electrode running along the analyte sensor to be transcutaneously implanted below the skin. The temperature sensor electrode would then be electrically coupled to a temperature measurement circuit within the on-body housing. The temperature measurements may be transmitted to the blood glucose meter upon request.

For manufacturability and cost-effectiveness, particularly when the on-body housing is intended to be disposable, it may be desirable to avoid the inclusion of a temperature sensor and/or control circuitry in the on-body housing. As such, in one embodiment, there is provided a blood glucose meter (or alternative hand-held measurement or analysis instrument) with a temperature measurement sensor and control system. In such embodiment, the temperature measurement sensor is provided on the permanent hand-held instrument to avoid disposing of the temperature measurement components when the on-body housing is disposed.

In one embodiment, for example, the hand-held instrument (e.g., glucose meter) may incorporate an infra-red (IR) laser thermometer. When the hand-held instrument is electrically coupled to the on-body housing, the IR beam can shine on a preselected area of the on-body housing and provide a temperature measurement. The preselected area may in turn provide a thermally conductive pathway to the skin surface. In another embodiment the IR beam can shine directly on the skin surface and provide a temperature measurement.

In another embodiment, the hand-held instrument (e.g., glucose meter) may incorporate temperature measurement electronics or circuitry for measuring a voltage produced by a thermistor/thermocouple in the on-body housing. When the hand-held instrument is electrically coupled to the on-body housing, the temperature measurement electronics measure such voltage from the thermistor/thermocouple. As such, the temperature sensor on the on-body housing remains disposable, however, the more expensive temperature measurement electronics or circuitry and control systems are not disposable.

Embodiments of the present disclosure provide real time analyte concentration determination from a self-powered sensor as desired or when needed by the patient or the user of the analyte monitoring system by physically touching or contacting the reader or the blood glucose meter device to the on-body housing placed on the skin surface of the user or the patient. Based on the physical touching or contacting, embodiments of the present disclosure include acquiring one or more signals (e.g., voltage levels) associated with the real time analyte concentration, or one or more signals (e.g., voltage levels) associated with monitored analyte concentration trend information (for example, the fluctuation of the monitored analyte concentration over the past three hour period, or over the past one hour period, or over the past five hour period, or other desirable time periods).

As discussed above, embodiments of the present disclosure include electrical contacts on the on-body housing placed on the skin surface and in signal communication with the analyte sensor such as self-powered glucose sensor described above, where the electrical contacts are formed of configured in one or more concentric circles such that any orientation of the reader or the blood glucose meter relative to the position of the on-body housing provides for proper contact between the probes on the reader or the blood glucose meter and the electrical contacts on the on-body housing to obtain the one or more signals corresponding to the real time monitored analyte level and/or monitored analyte concentration trend information.

Embodiments with the self-powered analyte sensor and the touch-based data acquisition described above provide for a compact on-body housing configuration as it obviates the need for a data transmission component (e.g., data transmitter such as radio frequency (RF) transmitter, or other communication components) and a power source such as a battery to provide power to the analyte sensor within the on-body housing. Further, the cost of manufacturing of the components of the analyte monitoring system including the on-body component may decrease without the need for data transmission component nor external power source such as the battery to power the analyte sensor.

In still another embodiment, where on body component includes an RF transmitter, monitored analyte concentration data may be captured and automatically transmitted at a predetermined time interval such as for example, once per minute, once every 5 minutes and so on, where the real time monitored analyte concentration data is wirelessly transmitted to the reader or the blood glucose meter over 1,400 times per day. Such embodiments also include alarms and/or alerts or notification functions to warn the user or the patient when the real time monitored analyte level crosses a threshold or a defined target levels so as to promptly and effectively take corrective actions.

In one embodiment, a system for determining real time analyte concentration includes an analyte sensor having a portion in fluid contact with an interstitial fluid under a skin layer; an on-body electronics including a housing coupled to the analyte sensor and configured for positioning on the skin layer, the on-body electronics housing including a plurality of electrical contacts provided on the housing; and a data analysis unit having a data analysis unit housing and including a plurality of probes provided on the data analysis unit housing, each of the plurality of probes on the data analysis unit housing configured to electrically couple to the respective one of the plurality of the electrical contacts on the on-body electronics housing when the data analysis unit is positioned in physical contact with the on-body electronics; wherein one or more signals on the plurality of probes on the data analysis unit housing corresponds to one or more of a substantially real time monitored analyte concentration level, monitored analyte concentration level over a predetermined time period, or a rate of change of the monitored analyte concentration level, or one or more combinations thereof.

In one embodiment, the analyte sensor is a self-powered sensor. When the self-powered sensor is inserted within interstitial fluid, for example, a current is generated by the sensor and provided to electronics on the OBU—e.g., to the circuit including the RC pairs.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. In one embodiment, the analyte sensor is a glucose sensor. In another embodiment, the analyte sensor is a ketone sensor.

In yet another embodiment, the plurality of electrical contacts on the on-body electronics housing are concentrically positioned on the on-body electronics housing. In some instances, one concentric electrical contact is a circular contact that is centered with respect to the center of the housing, and the other concentric electrical contacts are ring-shaped electrical contacts.

In a further embodiment, each of the plurality of electrical contacts on the on-body electronics housing are spaced apart by a predetermined distance relative to each other. The spacing between each adjacent electrical contact may be independent from one another. In some instances, each adjacent electrical contact is spaced the same distance from the other. In other instances, spacing between adjacent electrical contacts may vary from one another. It should be appreciated that the spacing implemented should align and correspond with the contacts on the reader to ensure proper contact when the reader is coupled to the on-body housing, irrespective of orientation of the reader on the OBU.

In another embodiment, the data analysis unit includes one of a reader or a blood glucose meter.

In yet another embodiment, the data analysis unit includes an output unit to output one or more indications related to the one or more of the substantially real time monitored analyte concentration level, the monitored analyte concentration level over a predetermined time period, the rate of change of the monitored analyte concentration level, or one or more combinations thereof.

In a further embodiment, the output unit includes one or more of a visual output unit, an audible output unit, or a vibratory output unit. The output units may facilitate proper operation of the device. In some instances, the output units provide alarms and/or reminders for the user—e.g., alarms for high or low glucose readings, rapid rises or declines in readings, reminders to take or log readings, reminders to take insulin or other medication, etc. Additional details regarding output units may be found in U.S. Provisional Application 61/451,488, the disclosure of which is incorporated herein by reference for all purposes.

In another embodiment, the predetermined time period includes about three hours. It should be appreciated that the time period may vary in different embodiments—e.g., longer or shorter than three hours. In some instances, the time period may be one or more days.

In yet another embodiment, the on-body electronics includes one or more data processing components to one or more filter, encode, store, analyze the one or more signals from the analyte sensor. For example, the OBU may also include a sensor circuit for obtaining signals from the sensor, a measurement circuit that converts sensor signals to a desired format, and a processing circuit that, at minimum, obtains signals from the sensor circuit and/or measurement circuit for communication to the reader. In some embodiments, the processing circuit may also partially or completely evaluate the signals from the sensor for communication to the reader. The processing circuit often includes digital logic circuitry. The OBU may also include a data storage unit for temporarily or permanently storing data from the processing circuit.

In a further embodiment, the one or more data processing components determines a three hour trend information based on analyte concentration monitored by the analyte sensor. It should be appreciated that the time period may vary in different embodiments—e.g., longer or shorter than three hours.

In another embodiment, a method includes positioning a portion of an analyte sensor in fluid contact with an interstitial fluid under a skin layer; positioning an on-body electronics housing coupled to the analyte sensor on the skin layer, the on-body electronics housing including a plurality of electrical contacts provided on the housing; and contacting a plurality of probes provided on a data analysis unit housing to the respective one of the plurality of the electrical contacts on the on-body electronics housing to receive one or more analyte sensor related signals corresponding to one or more of a substantially real time monitored analyte concentration level, monitored analyte concentration level over a predetermined time period, or a rate of change of the monitored analyte concentration level, or one or more combinations thereof.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A system for determining analyte concentration, comprising:

an analyte sensor having a portion in fluid contact with an interstitial fluid under a skin layer;

an on-body electronics unit including a housing having a plurality of electrical contacts concentrically positioned on the on-body electronics housing, the on-body electronics unit coupled to the analyte sensor, comprising a first and second resistor-capacitor (RC) pair in series and electrically coupled to the analyte sensor such that a first voltage across the first RC pair represents a real-time current analyte concentration level, a second voltage across the second RC pair represents an average analyte concentration level over a period of time, and a difference between the first and second voltages represents a real-time trending of the analyte concentration level; and a data analysis unit in communication with the on body electronics unit.

2. The system of claim 1, wherein the analyte sensor is a self powered sensor.

3. The system of claim 1, wherein the analyte sensor is a glucose sensor.

4. The system of claim 1, wherein data analysis unit comprises a housing comprising a plurality of probes provided on the data analysis unit housing, each of the plurality of probes on the data analysis unit housing configured to electrically couple to the respective one of the plurality of the electrical contacts on the on-body electronics housing when the data analysis unit is positioned in physical contact with the on-body electronics.

5. The system of claim 1, wherein each of the plurality of electrical contacts on the on-body electronics housing are spaced apart by a predetermined distance relative to each other.

6. The system of claim 1, wherein the data analysis unit includes one of a reader or a blood glucose meter.

7. The system of claim 1, wherein the data analysis unit includes an output unit to output one or more indications related to the one or more of the substantially real time monitored analyte concentration level, the monitored analyte concentration level over a predetermined time period, the rate of change of the monitored analyte concentration level, or one or more combinations thereof.

8. The system of claim 7, wherein the output unit includes one or more of a visual output unit, an audible output unit, or a vibratory output unit.

9. The system of claim 1, wherein the predetermined time period includes about three hours.

10. The system of claim 1, wherein the on-body electronics includes one or more data processing components to one or more filter, encode, store, analyze the one or more signals from the analyte sensor.

11. The system of claim 10, wherein the one or more data processing components determines a three hour trend information based on analyte concentration monitored by the analyte sensor.

12. The system of claim 1, wherein the data analysis unit calculates the difference between the first voltage and the second voltage to determine the real-time trending of the analyte concentration level.

13. The system of claim 1, wherein the data analysis unit includes an output unit that outputs a first indication of the real-time current analyte concentration level and a second indication of the real-time trending of the analyte concentration level.

14. The system of claim 1, wherein one or more signals on the plurality of probes on the data analysis unit housing comprises the first voltage and the second voltage and corresponds to one or more of a substantially real time monitored analyte concentration level, monitored analyte concentration level over a predetermined time period, or a rate of change of the monitored analyte concentration level, or one or more combinations thereof.

* * * * *